United States Patent [19]

Fenole et al.

[11] 4,069,817
[45] Jan. 24, 1978

[54] BODY WASTE DETECTING DEVICE

[76] Inventors: Joseph E. Fenole, 2014 Jamestown Way, Oxnard, Calif. 93030; Jerry E. Wells, P.O. Box 5796, Oxnard, Calif. 93031; Bernard C. Chicoine, P.O. Box 1435, Ventura, Calif. 93001

[21] Appl. No.: 717,478

[22] Filed: Aug. 25, 1976

[51] Int. Cl.² .............................................. A61B 19/00
[52] U.S. Cl. .............................. 128/138 A; 200/61.05; 340/235
[58] Field of Search ....................... 128/138 A, 138 R; 340/235, 279; 200/61.05

[56] References Cited

U.S. PATENT DOCUMENTS

| | | | |
|---|---|---|---|
| 2,726,294 | 12/1955 | Kroening et al. | 200/61.05 |
| 2,735,907 | 2/1956 | Inman | 200/61.05 |
| 3,245,068 | 4/1966 | Wegryn et al. | 340/235 |
| 3,530,855 | 9/1970 | Balding | 128/138 A |
| 3,614,763 | 10/1971 | Yannuzzi | 340/279 |
| 3,696,357 | 10/1972 | Kilgore | 340/235 |
| 3,778,570 | 12/1973 | Shuman | 200/61.05 |
| 3,864,676 | 2/1975 | Macias | 128/138 A X |

FOREIGN PATENT DOCUMENTS

| | | | |
|---|---|---|---|
| 1,174,346 | 12/1969 | United Kingdom | 128/138 A |
| 1,251,964 | 11/1971 | United Kingdom | 128/138 A |

OTHER PUBLICATIONS

Seiger et al., "A Practical . . . Diaper Signal", J. of Pediatrics, vol. 28, No. 6, June, 1946, pp. 733-736.

Primary Examiner—Robert W. Michell
Assistant Examiner—Lee S. Cohen
Attorney, Agent, or Firm—Ralph B. Pastoriza

[57] ABSTRACT

The detecting device is used for incontinent patients in hospitals and care homes and takes the form of an elongated flexible strip arranged to be positioned beneath a patient in a wheelchair or bed. The strip has two conductive paths printed on it which are electrically bridged by body waste such as urine to decrease the resistance between the two paths. A detecting circuit in a casing which may be clipped to a portion of a wheelchair frame or bed frame is responsive to the change in resistance to energize a small directional light and thus provide a discreet signal that the patient needs attention.

3 Claims, 5 Drawing Figures

BODY WASTE DETECTING DEVICE

This invention relates generally to moisture responsive signalling devices and particularly such devices of the type to detect urine and similar body wastes to alert hospital personnel that a patient needs attention.

BACKGROUND OF THE INVENTION

Moisture responsive devices of the type under consideration are well known in the art and a large number of patents have issued on various forms. Basically, most of these presently available devices utilize a fairly large rectangular or square or even circular shaped pad arranged to be positioned beneath a patient. This pad normally includes two distinct circuits made up of wires or even printed conductive paths sandwiched together in such a manner that wetting of the pad by a patient bridges adjacent portions of the circuits together. An appropriate electrical trigger circuit connects to the two paths and the change in resistance resulting from the presence of moisture causes the circuit to trigger an appropriate alarm.

Notwithstanding the large amount of prior art and technical information available relating to devices of the foregoing type, there are still disadvantages in their use and thus room for improvement. More particularly, as described the devices generally comprise a relatively large pad and where a wire mesh or physical wires themselves are employed for the conductive circuits within the pad, the pad itself can become bulky and of appreciable thickness. Thus, the same is not always comfortable when disposed beneath a patient. Moreover, the relatively large areas of such pads makes it difficult to clean the same.

Another problem involved is that of the various alarms used to signal the fact that a patient needs attention. Some of these alarms take the form of bells or buzzers while others may constitute lights which are readily visible. As a result, while a patient may be given relatively quick attention after an accidental uncontrolled wetting, other patients in the area and even other doctors and nurses other than his own personal nurse and physician are made cognizant of the fact that he has wet his bed by means of the signalling device. This attention can cause considerable embarrassment to the patient himself.

BRIEF DESCRIPTION OF THE PRESENT INVENTION

With the foregoing considerations in mind, the present invention contemplates a vastly improved body waste detecting device of unique construction such as to overcome the foregoing problems associated with presently available devices.

More particularly, the present invention contemplates the provision of an elongated flexible electrically insulating strip preferably of thin plastic material as opposed to a rectangular or square pad. This strip has conductive paths printed on its surface in an appropriate arrangement such that any portion of the surface which becomes moistened because of body waste bridges the conductive path. A small compact casing houses an electrial circuit and also includes a fastening means for manually supporting the casing to a portion of a wheelchair frame or bed frame, there being provided a separable plug arrangement to connect the conductive paths of the strip to the circuit within the casing. The overall structure is thus very portable and extremely easy to use.

The circuit in the casing is responsive to a change in resistance of the conductive paths in the elongated strip to trigger energization of a directional light source which will normally only be visible to those in attendance. No audible sound results so that the patient can maintain his dignity and yet the light source itself is sufficient to alert necessary personnel acquainted with the system to give the patient immediate attention.

The design of the elongated strip itself is such as to be hardly noticeable by the patient when positioned beneath the patient. The connecting means between the strip and the casing incorporating the circuit can be easily connected or disconnected so that the strip itself can be washed without any problems.

BRIEF DESCRIPTION OF THE DRAWINGS

A better understanding of this invention will be had by now referring to a preferred embodiment thereof as illustrated in the accompanying drawings in which.

DETAILED DESCRIPTION OF THE PREFERRED EMBODIMENT

Figure 1:
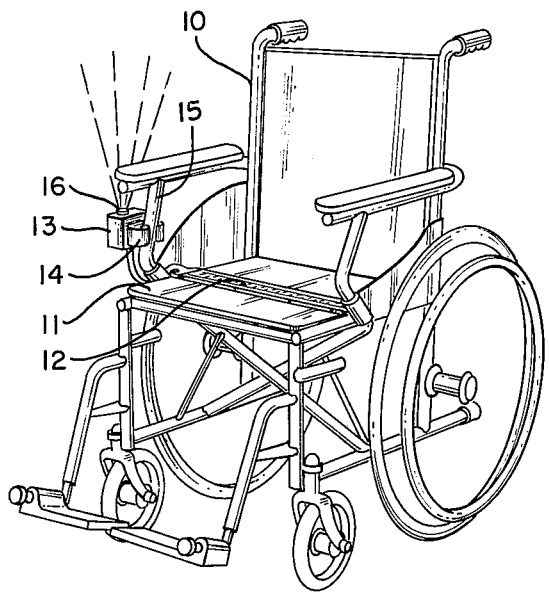
FIG. 1 is a perspective view of a wheelchair to which the body waste detector of this invention has been secured to detect body waste from any patient seated in the chair.

Referring first to FIG. 1 there is shown a wheelchair 10 having a seat 11 across which has been positioned an elongated flexible electrically insulating plastic strip 12. This strip connects to an appropriate circuit means within a casing 13 arranged to be fastened to the wheelchair in a convenient position as by a spring clip 14. For example, the spring clip 14 is shown connnected to the frame tube portion 15 beneath the arm rest.

When a patient is seated in the chair should he urinate or otherwise dispel body waste, the resulting moisture on the strip 12 will bridge conductive paths all as will become clearer as the description proceeds to trigger the electrical circuit in the casing 14 and energize a directional light. This directional light is indicated at 16 in FIG. 1 and positioned to shine in a generally upward direction. Any passing nurses or other attendants can discreatly observe this light while other patients and personnel in the general environment will not be aware of its energization. As a consequence, the patient will not be embarrassed to the extent that he otherwise might.

Figure 2:
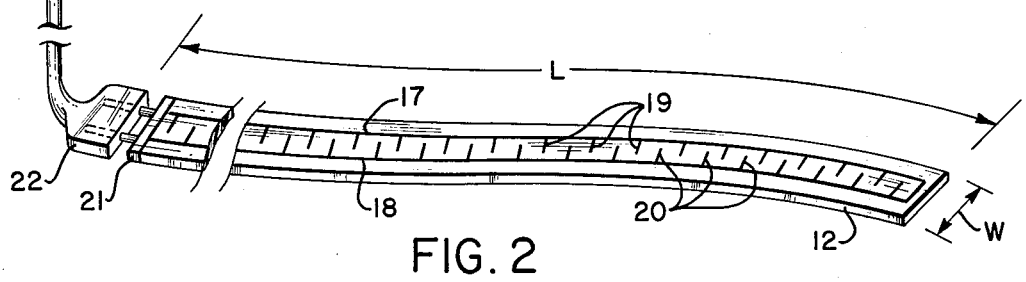
FIG. 2 is a greatly enlarged perspective view of the body waste detector itself.

Referring now to FIG. 2, details of the body waste detector utilized on the wheelchair of FIG. 1 will be described. As shown, the elongated strip 12 has a length L, and a width W. In all embodiments, the length L is made at least equal to 15 times the width W and preferably longer. As an example, the width of the strip might be 2½ centimeters or approximately one inch while the length might lie somewhere between 45 and 70 centimeters. The thickness of the strip as will be described subsequently is made as small as possible, the width dimension W being at least equal to 20 times the thickness dimension of the strip.

The strip itself as stated is of electrically insulating material and may constitute "Mylar".

A first conductive longitudinal path 17 is provided on the surface of the strip running adjacent to and parallel with one longitudinal edge of the strip as shown. Similarly, a second conductive longitudinal path 18 runs adjacent to and parallel with the opposite longitudinal edge of the strip. Each of the conductive paths has a plurality of connected conductive transverse paths extending towards the other longitudinal path as indicated at 19 and 20 respectively in a staggered manner and terminating short of the other path to define inter digitated fingers insulated from each other.

The initial portions of the conductive paths 17 and 18 connect to a plug 21 receivable in a socket 22 connected to the circuit means within the casing 13 as by line 23.

Figure 3:
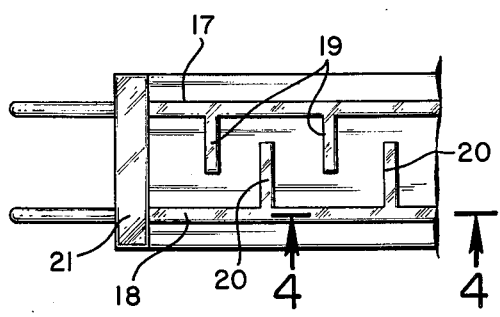
FIG. 3 is an enlarged fragmentary plan view of an end of the strip portion of the device of FIG. 2.

Referring now to FIG. 3, the configuration of the paths 17 and 18 and the conductive transverse paths 19 and 20 will be evident. These paths are in insulated spaced relationship to each other, the spacing being such that a given amount of waste material or moisture is required to effect a bridging between the paths.

Figure 4:
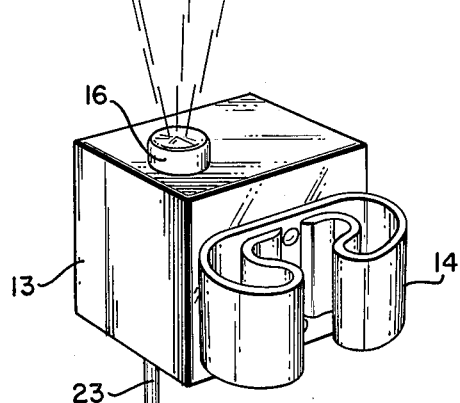
FIG. 4 is a greatly enlarged fragmentary cross section taken in the direction of the arrows 4—4 of FIG. 3.
Figure 4:
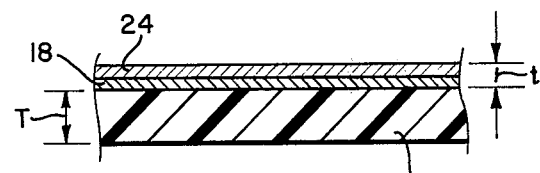

FIG. 4 shows in greatly magnified form the relative thicknesses of the Mylar supporting plastic strip and conductive paths. In the preferred embodiment, the first and second conductive longitudinal paths and corresonding conductive transverse paths are provided with a protective conductive coating indicated at 24 to prevent corrosion. In a specific preferred embodiment, the conductive paths such as 18 may comprise a copper coating while the protective covering coating 24 may comprise nickel. The thickness of the underlying plastic strip is indicated at T while the combined thicknesses of the conductive paths and overlying coatings is indicated at t. As stated, the thickness T is fairly small compared with the width W of the strip and thus the strip itself can be quite flexible and conform to the contour of the seat 11, for example, of the wheelchair of FIG. 1 when disposed on the seat beneath a patient.

Figure 5:
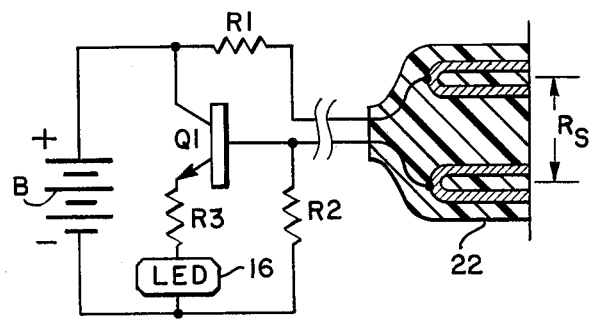
FIG. 5 is a cross section of a socket and circuit means constituting part of the structure of FIG. 2.

FIG. 5 illustrates a typical circuit means for energizing the directional light source 16. In FIG. 5, the plug portion 22 described briefly in FIG. 2 is illustrated in cross section. Appropriate conductors connect from the conductive receiving sockets of the plug 22 through resistances R1 and R2 across a battery or appropriate voltage source B all housed within the casing 13. Also included is a switching transistor Q1 with its collector connected between the resistance R1 and positive terminal on the battery B and its emitter connected through a resistance R3 to the directional light source 16 which might constitute a light emitting diode (LED). The other side of the light emitting diode connects to the negative side of the battery B.

With the foregoing circuit, it will be evident that any resistance Rs between the conductive paths 17 and 18 of FIG. 3 when the plug 21 is inserted in the socket 22 will be in series with the resistance R1 and R2 of the circuit shown in FIG. 5. A change in the resistance Rs which results when moisture contacts the surface of the conductive paths on the strip will result in a change in the division of the voltage across the resistance R1, Rs and R2 supplied by the battery B, the voltage applied to the base of the transistor Q1 between the junction of the resistance Rs and R2 increasing when the resistance Rs decreases by a given amount thereby turning on the transistor Q1 and applying voltage from the battery B across the light emitting diode 16 through resistance R3. Energization of the light emitting diode will thus provide a signal that moisture is present and the patient needs attention.

Any other appropriate circuit could be utilized in place of that of FIG. 5. The circuit of FIG. 5 is economical to manufacture and can be formed in a compact configuration. Further, by using the simple battery of, for example, 9 volts, there is not present any danger of electrical shock and the like.

OPERATION

The operation of the body waste detector of this invention will be evident from the foregoing description. As described earlier, the casing 13 may be clipped to any convenient frame portion of a wheelchair or a bed, the conducting line 23 to the strip 12 being made of any desired length so that the strip portion itself can be conveniently positioned beneath a patient in the chair or in a bed.

Any urine or other body waste from the patient contacting the top surface of the strip will decrease the resistance between the adjacent conductive paths thereby causing the directional light 16 to be energized and thus alerting a nurse or attendant in a discreet manner.

As also described heretofore, it is easy to manually unplug the plug 21 from the socket 22 for purposes of cleaning the strip itself.

From the foregoing description, it will be evident that the present invention has provided an improved moisture responsive device of the type used to detect body wastes wherein certain disadvantages of presently available devices are overcome.

What is claimed is :

1. A body waste detecting device including, in combination:
   a. an elongated flexible electrically insulating plastic strip having a length L, width W and thickness T, wherein L is at least 15 W and W is at least 20 T;
   b. a first conductive longitudinal path on the surface of said strip running adjacent to and parallel with one longitudinal edge of the strip;
   c. a second conductive longitudinal path on said surface of said strip adjacent to and running parallel with the opposite longitudinal edge of said strip, each of the conductive paths having a plurality of connected conductive transverse paths extending towards the other longitudinal path in a staggered manner and terminating short of the other path to define inter-digitated fingers insulated from each other;
   d. a protective conductive coating overlying each of the conductive paths;
   e. a casing incorporating a directional light source, a battery, and circuit means connected between the battery and light source;
   f. manually attachable fastening means on the exterior of said casing for supporting the casing to a frame portion of a wheelchair or bed; and,
   g. electrical connecting means for connecting said first and second conductive longitudinal paths to said circuit means in said casing, said circuit means being responsive to a change in resistance resulting from body waste contacting a surface portion of said strip in a manner to bridge any portion of the first and second conductive longitudinal paths and corresponding conductive transverse paths to energize said light source, whereby said casing may be easily attached to a wheelchair or bed frame and said strip disposed beneath a patient in said chair or bed, energization of said light source providing a discreet indication of the presence of body waste from said patient.

2. A device according to claim 1, in which said electrical connecting means comprises a two-prong plug and socket so that said strip can be easily disconnected from said casing, cleaned and reconnected as required.

3. A device according to claim 2, in which said first and second conductive longitudinal paths and corresponding connected conductive transverse paths comprise copper and in which said protective conductive coating comprises nickel.

* * * * *